Figure 1:
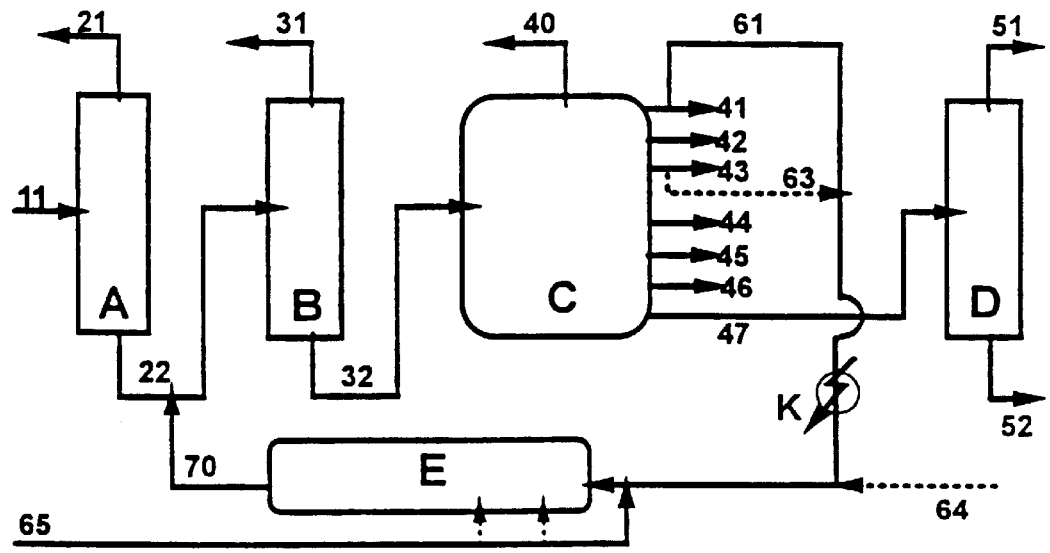

United States Patent

Köll, deceased et al.

[11] Patent Number: 6,013,801
[45] Date of Patent: Jan. 11, 2000

[54] METHOD FOR PRODUCING AMINOETHYLETHANOLAMINE AND/OR HYDROXYETHYL PIPERAZINE

[75] Inventors: Juhan Köll, deceased, late of Stenungsund, by Mall Koll, legal representative; Magnus Frank, Göteborg, both of Sweden

[73] Assignee: Akzo Nobel N.V., Arnhem, Netherlands

[21] Appl. No.: 08/875,871

[22] PCT Filed: Jan. 11, 1996

[86] PCT No.: PCT/EP96/00207

§ 371 Date: Oct. 30, 1998

§ 102(e) Date: Oct. 30, 1998

[87] PCT Pub. No.: WO96/24576

PCT Pub. Date: Aug. 15, 1996

[30] Foreign Application Priority Data

Feb. 8, 1995 [SE] Sweden .................................. 9500444

[51] Int. Cl.[7] .................. C07D 295/88; C07C 213/04
[52] U.S. Cl. ................................... 544/401; 564/503
[58] Field of Search .............................. 544/401; 564/503

[56] References Cited

U.S. PATENT DOCUMENTS

| | | | |
|---|---|---|---|
| 4,338,443 | 7/1982 | Brennan et al. | 544/401 |
| 4,590,223 | 5/1986 | Arai et al. | 544/401 X |
| 5,455,352 | 10/1995 | Huellmann et al. | 544/401 |

FOREIGN PATENT DOCUMENTS

| | | | |
|---|---|---|---|
| 0 354 993 | 2/1990 | European Pat. Off. | C07C 213/06 |
| 2013 676 | 1/1972 | Germany | C07D 51/64 |
| 27 16946 | 10/1978 | Germany | C07C 89/02 |
| 206 670 | 2/1984 | Germany . | |
| 1512967 | 10/1989 | Russian Federation | C07C 91/12 |

OTHER PUBLICATIONS

Ludwig Knorr und Henry W. Brownadon: Ueber Alkoholbasen aus Aethylendiamin und uber das Aethylenbismorpholin, Dec. 11, 1902 pp. 4470–4473.

*Primary Examiner*—Michael G. Ambrose
*Attorney, Agent, or Firm*—Ralph J. Mancini

[57] ABSTRACT

A method for preparing aminoethylethanolamine, and/or hydroxyethylpiperazine is described. Reaction of ethylene oxide with ethylendiamine, piperazine, or a mixture of both produces these compounds. The process is integrated into a distillation plant for processing the amination product flow obtained from the reaction of monoethanolamine with ammonia

12 Claims, 1 Drawing Sheet

METHOD FOR PRODUCING AMINOETHYLETHANOLAMINE AND/OR HYDROXYETHYL PIPERAZINE

The present invention relates to a method for producing aminoethylethanolamine, hydroxyethyl piperazine or both these compounds by continuously ethoxylating ethylenediamine, piperazine or a mixture thereof in an excess of ethylenediamine and piperazine. The resulting ethoxylation product flow is then processed by distillation in a distillation plant for processing an amination product flow obtained in the amination of monoethanolamine with ammonia.

It is long since known, for instance from Knorr et al, Ber. 35 (1902), p. 4470, to produce aminoethylethanolamine by reacting ethylene oxide with ethylenediamine at room temperature and in the presence of considerable amounts of water. The reaction is carried out in an excess of ethylenediamine in order to avoid the formation of higher adducts, such as N,N'-bis(2-hydroxyethyl)-ethylenediamine. DE-A-2,716,946 discloses a discontinuous method for producing aminoethylethanolamine by reacting ethylenediamine with ethylene oxide at a temperature of 100–120° C. and in the presence of water in a specially-developed reaction apparatus. Patent Specification SU-A-1,512,967 discloses the production of N,N'-bis(2-hydroxyethyl)-ethylenediamine by ethoxylating ethylenediamine with ethylene oxide in a molar ratio of 1:2 at a temperature of 40–50° C. and in an approximately 20% aqueous solution. This reaction generates a great number of by-products. Patent Publication EP-A-354 993 proposes that amines containing reactive hydrogen atoms are reacted with ethylene oxide and/or propylene oxide at an elevated temperature, conveniently a temperature of 130–180° C., at a pressure above atmospheric and in the absence of any solvent but in the presence of a catalytic amount of alkali metal hydroxide and/or alkali metal alkoxide.

It is known from DE-A-2,013,676 to react, in a first step, ethylenediamine with ethylene oxide in the absence of a catalyst, and to react, in a second step, the formed higher condensation products in the presence of hydrogen (and optionally ammonia) and a hydration catalyst to piperazine, hydroxyethyl piperazine and N-aminoethyl piperazine.

It is further known that the production of ethylenediamine by the amination of monoethanolamine with ammonia inter alia results in minor amounts of ethylenediamine and piperazine substituted with one or more hydroxyethyl groups. The reaction mixture obtained in the amination is then separated by multistep distillation.

There are many difficulties associated with the production of aminoethylethanolamine and hydroxyethyl piperazine. Thus, one problem is that the ethoxylation of ethylenediamine results in the formation of a number of undesirable by-products, such as di-, tri- or tetra (hydroxyethyl)-ethylenediamine which, along with unreacted ethylenediamine and ethylene oxide as well any water present have to be separated from the aminoethylethanolamine, usually by vacuum distillation. The use of water as catalyst results in the formation of a high-boiling azeotrope of ethylenediamine and water, which is difficult to break. The ethoxylation of piperazine results in the formation of not only hydroxyethyl piperazine but also di-(hydroxyethyl)-piperazine. The resulting product mixture is usually separated by vacuum distillation. If use is made of catalysts which wholly or partly are dissolved in the reactants, also these should be removed prior to the processing of the reaction mixture. In reactions above 100° C., ethylene oxide reacts also with the water present to form ethylene glycol, which results in ethylene oxide losses and further separation problems.

The object of the present invention is to produce aminoethylethanolamine and/or hydroxyethyl piperazine in such a manner as to simplify the purification process. Another object of the invention is that the reaction should be carried out continuously, so as to avoid the problems associated with a reaction batchwise. Further objects of the invention are to achieve high yields of the desirable compounds and to enable use of reactants which are not necessarily pure.

It has now been found that these objects are attained by reacting ethylenediamine, piperazine or a mixture thereof with ethylene oxide in the presence of a catalyst, the reaction process involving the steps of i) continuously reacting ethylenediamine and/or piperazine with 0.05–0.5 mole of ethylene oxide, preferably 0.1–0.3 mole, per mole of ethylenediamine and/or piperazine in the presence of a catalyst, ii) introducing the resulting ethoxylation product flow into a distillation plant designed for processing an amination product flow obtained by aminating monoethanolamine with ammonia, and iii) distilling the ethoxylation product flow in the distillation plant while recovering aminoethylethanolamine and/or hydroxyethyl piperazine.

Preferably, the catalyst employed consists of water or a solid catalyst which is not dissolved during the ethoxylation reaction. Conveniently, the ethoxylation product flow is introduced into the distillation plant before the first column where, in the distillation of the amination product flow, a compound or mixture is separated which contains a compound forming part of the ethoxylation product flow. As a result of the mode of implementation of the method according to the invention, the reaction products can be processed in a plant intended for the production of ethyleneamines by catalytic amination of monethanolamine with ammonia, since the ethoxylated products found in the ethoxylation product flow are present also in the amination product flow obtained in catalytic amination of monoethanolamine with ammonia.

In one preferred mode of implementation, it has been found highly suitable to conduct amination and ethoxylation in parallel and to join the ethoxylation product flow and the amination product flow in the distillation plant. Owing to the higher content of aminoethylethanolamine and/or hydroxyethyl piperazine in the thus-joined product flows, it has, in addition, been found that the recovery of ethylenediamine from the azeotrope of ethylenediamine and water is facilitated.

In another preferred mode of implementation, ethylenediamine and/or piperazine are drawn off in the form of a product flow from the distillation plant where the ethoxylation product flow and the amination product flow are being processed jointly. Such a product flow may wholly or partly consist of the azeotrope of ethylenediamine and water (optionally containing piperazine), in which case the water will serve as catalyst in the ethoxylation reaction. An ethylenediamine-containing fraction, which has not yet been fully processed, may then be used as reactant.

If water, wholly or partly, is used as catalyst, the ethoxylation reaction is carried out at a temperature of 20–95° C., preferably 40–80° C. Under such conditions, it has been found possible to attain a satisfactory ethoxylation rate as well as a high selectivity for ethoxylation of the reactive hydrogen atoms of the amine compounds, there being practically no formation of glycols or any ethoxylation of hydroxyl groups. If the reaction is carried out in the absence of water, the reaction temperature suitably is 20–150° C., preferably 40–120° C. If use is made of a solid ethoxylation catalyst which is not soluble during the reaction, additional process steps for removing the catalyst can be avoided. Examples of suitable solid catalysts are acid ion exchangers, acid zeolites, acid clays and Lewis acids. The term solid catalysts also includes liquid catalysts that are bound to a solid carrier. It is further possible to use a solid ethoxylation catalyst in combination with water.

The ethoxylation of ethylenediamine and piperazine to aminoethylethanolamine and hydroxyethyl piperazine, respectively, implies that only one of the four and two reactive hydrogen atoms of ethylenediamine and piperazine, respectively, react with ethylene oxide. According to the invention, this problem is solved by performing the reaction with an considerable excess of ethylenediamine and/or piperazine. In the method, use may also be made of ethylenediamine and/or piperazine containing minor amounts of other compounds with reactive hydrogen atoms obtained from the amination plant. The ethoxylates formed from these compounds, as well as unreacted ethylenediamine and piperazine can be recovered as pure products or as a high-boiling distillation residue, optionally together with the corresponding components of the amination flow.

A suitable starting product for ethoxylation is, for instance, an ethylenediamine fraction which contains at least 95% by weight of ethylenediamine and which has been obtained from the distillation plant. If the fraction is water-free, the reaction is preferably carried out in the presence of a solid catalyst in a water-free environment. It is also suitable to ethoxylate a mixture of ethylenediamine and piperazine, in which case the two amine compounds may have been obtained in the distillation plant. Such a product mixture may contain 60–100% by weight of ethylenediamine, preferably 80–95% by weight, and 0–40% by weight of piperazine, preferably 0–20% by weight. Use is preferably made of the ethylenediamine azeotrope formed when reacting monoethanolamine and ammonia. Additional ethylenediamine and/or piperazine may also be added to the azeotrope, as may additional amounts of water. Conveniently, such a product mixture contains 55–95% by weight of ethylenediamine, preferably 70–90% by weight; 1–30% by weight of water, preferably 10–20% by weight; and 0–40% by weight of piperazine, preferably 0–10% by weight.

By performing the ethoxylation of ethylene diamine and/or piperazine in the special manner described and by performing the processing in a distillation plant for amination products obtained in the amination of monoethanolamine with ammonia, a simple and cost-effective mode of production of aminoethyl-ethanolamine and/or hydroxyethyl piperazine is obtained.

Figure 2:
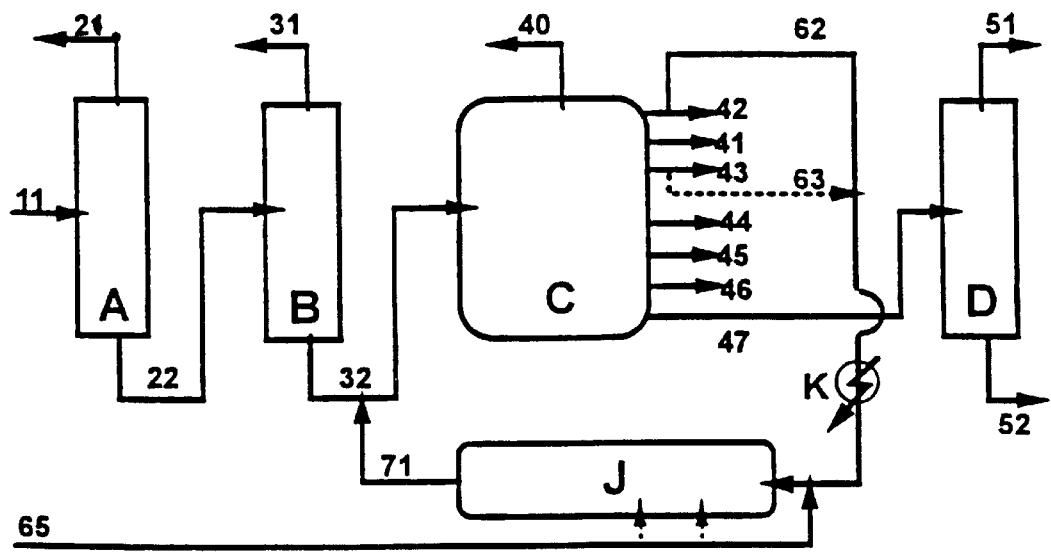

Appended FIGS. 1 and 2 schematically illustrate two examples of how the ethoxylation process can be integrated with a distillation plant for processing an amination product flow obtained in the amination of monoethanolamine with ammonia. The following abbreviations are used in the description of the Figures as well as in the Examples below.

| | | |
|---|---|---|
| AEEA | = | Aminoethylethanolamine |
| DETA | = | Diethylenetriamine |
| EDA | = | Ethylenediamine |
| EO | = | Ethylene oxide |
| HEP | = | Hydroxyethyl piperazine |

-continued

| | | |
|---|---|---|
| MEA | = | Monoethanolamine |
| PIP | = | Piperazine |

FIG. 1 schematically illustrates an arrangement for integrated ethoxylation of EDA and/or PIP to AEEA and/or HEP. A, B and D are columns in a distillation plant for processing an amination product flow obtained in the amination of M with ammonia. C is a system of distillation columns for separating various products, and E is a reactor for ethoxylating EDA and/or PIP. An amination product flow 11 is introduced into the distillation column A, where ammonia is separated. In the distillation column B. The main part of the water present in the amination product flow is separated and drawn off through a conduit 31. The remaining amines are conducted through a conduit 32 to the distillation system C, where an EDA-water azeotrope, EDA, PIP, DETA, AEP and HEP are separated via the conduits 41, 42, 43, 44, 45 and 46, respectively. Usually, the azeotrope contains 80–90% by weight of EDA, 0–5% by weight of PIP and 10–20% by weight of water. A flow 46 of high-boiling amines leaves the system of columns C. In the column D, these high-boiling amines are, by distillation, separated into AEEA, which is drawn off through a conduit 51, and a bottom fraction, which is drawn 5 off through a conduit 52. The azeotrope 41 is, wholly or partly and after optional cooling to a suitable reaction temperature in a cooler K, conducted through a conduit 61 to the ethoxylation reactor E. If so desired, more water can be added to the azeotrope through a conduit 64, and more piperazine may be added 10 through a conduit 63. Ethylene oxide is introduced into the reactor E through a conduit 65, suitably in several places. The reaction mixture formed in the ethoxylation reactor E, which in addition to EDA and water contains EDA adducts and/or PIP adducts, is joined with the ammonia-free amination product flow 22 for distillation.

FIG. 2 shows an alternative arrangement, which enables the production of more AEEA than is possible when using the EDA-water azeotrope only. Like components as in FIG. 1 are identified by like designations. In view of the ethoxylation, part of the flow 42, which consists of EDA, is conducted, via a conduit 62, to an ethoxylation reactor J, which contains an acid ion exchanger as catalyst. No water need be added. Since the reaction mixture contains EO and an excess of EDA, only EDA ethoxylates are, apart from EDA, obtained in the ethoxylation product flow 71. Then, the ethoxylation product flow 71 is joined with a flow 32 from the distillation column B, which as a result is subjected to less load.

A great number of arrangements of the distillation plant and its integration with the ethoxylation reactor are conceivable within the scope of the invention. For instance, the flow 41 in FIG. 2, i.e. the azeotrope of ethylenediamine and water, may wholly or partly be introduced into the ethoxylation reactor J. If so, the ethoxylation product flow should, however, be joined with the ammonia-free amination product flow 22 from the column A.

The invention will now be further illustrated with the aid of two Examples.

EXAMPLE 1

A flow leaving a distillation plant according to FIG. 1 and containing 72% of EDA, 4% of PIP and 23% of water was cooled to 40° C. and introduced into an ethoxylation reactor with a static mixer. Ethylene oxide in a molar ratio of EDA to EO of 1:0.17 was then added to the reactor in several steps. In the reaction, the temperature rose to 90–95° C. The ethoxylation product flow from the reactor contained 56.5% of EDA, 2.5% of PIP, 19.5% of water, 17% of AEEA, 3% of HEP and 1.5% of other reaction products. All the ethylene oxide had reacted. 95% of the EDA spent and 93% of the PIP spent had reacted to AEEA and HEP. 79% of the EQ supplied had reacted to AEEA, while 11% thereof had reacted to HEP and 10% thereof had reacted to other products. The resulting ethoxylation product flow was joined with the amination product flow for distillation. In processing in accordance with FIG. 1, the additions of both AEEA and HEP were found in the amounts expected from the analysis.

EXAMPLE 2

An EDA-containing flow (more than 99.5% by weight of EDA; cooled to 50° C.) in accordance with FIG. 2 was introduced into an ethoxylation reactor which contained a solid catalyst consisting of an ion exchanger in sulphonic-acid form. In addition, 0.105 mole of ethylene oxide per mole of EDA was supplied to the reactor in several steps, and the reaction was carried out at about 75° C. The ethoxylation flow leaving the reactor contained 85% of EDA, 14% of AEEA and 1% of other reaction products. All the EQ had reacted. More than 99% of the EDA spent had reacted to AEEA. The resulting ethoxylation product flow was joined with the amination product flow for distillation. In processing in accordance with FIG. 2, the addition of AEEA was found in the amount expected from the analysis.

We claim:

1. A method for producing aminoethylethanolamine, hydroxyethyl piperazine, or both aminoethylethanolamine and hydroxyethyl piperazine by ethoxylating ethylenediamine, piperazine or both ethylenediamine and piperazine with ethylene oxide in the presence of a catalyst, said method comprising continuously reacting ethylenediamine, piperazine, or both ethylenediamine and piperazine with 0.05–0.5 mole of ethylene oxide per mole of ethylenediamine, piperazine, or both ethylenediamine and piperazine, introducing the resulting ethoxylation product flow into a distillation plant designed for processing an amination product flow obtained by aminating monoethanolamine with ammonia, and distilling the ethoxylation product flow in the distillation plant while recovering aminoethylethanolamine, hydroxyethyl piperazine or both aminoethylethanolamine and hydroxyethyl piperazine.

2. The method of claim 1, wherein said method is performed in the presence of water as catalyst at a temperature of 20–95° C.

3. The method of claim 1 wherein said method is performed in the absence of water but in the presence of a solid catalyst, which is not dissolved during the reaction, and at a temperature of 20–150° C.

4. The method of claim 1 wherein the ethoxylation product flow is introduced into the distillation plant before the first column where, in the distillation of the amination product flow, a compound or mixture is separated which contains a compound forming part of the ethoxylation product flow.

5. The method of claim 1 wherein the ethoxylation product flow is joined with the amination product flow and this combined product flow is jointly distilled in the distillation plant.

6. The method of claim 1 which comprises ethoxylating an ethylenediamine fraction which contains at least 95% by weight of ethylenediamine and which has been obtained from the distillation plant.

7. The method of claim 1 which comprises ethoxylating a product mixture which contains 55–95% by weight of ethylenediamine 1–30% by weight of water; and 0–20% by weight of piperazine.

8. The method of claim 3 which comprises ethoxylating a product mixture which contains 60–100% by weight of ethylenediamine; and 0–40% by weight of piperazine.

9. The method of claim 2 wherein said temperature is in the range of 40–80° C.

10. The method of claim 3 wherein said temperature is in the range of 40–120° C.

11. The method of claim 7 wherein said product mixture contains 70–90% by weight ethylenediamine; 10–20% by weight water and 0–10% by weight piperazine.

12. The method of claim 8 wherein the product mixture contains 80–95% by weight ethylenediamine; and 5–20% piperazine.

* * * * *